US010780199B2

(12) United States Patent
Gilman

(10) Patent No.: US 10,780,199 B2
(45) Date of Patent: *Sep. 22, 2020

(54) METHODS OF APPLYING A HYDROPHILIC COATING TO A SUBSTRATE, AND SUBSTRATES HAVING A HYDROPHILIC COATING

(71) Applicant: Hollister Incorporated, Libertyville, IL (US)

(72) Inventor: Thomas H. Gilman, Spring Grove, IL (US)

(73) Assignee: Hollister Incorporated, Libertyville, IL (US)

( * ) Notice: Subject to any disclaimer, the term of this patent is extended or adjusted under 35 U.S.C. 154(b) by 143 days.

This patent is subject to a terminal disclaimer.

(21) Appl. No.: 14/886,901

(22) Filed: Oct. 19, 2015

(65) Prior Publication Data

US 2016/0038652 A1    Feb. 11, 2016

Related U.S. Application Data

(60) Continuation of application No. 13/748,842, filed on Jan. 24, 2013, now abandoned, which is a continuation of application No. 13/243,942, filed on Sep. 23, 2011, now Pat. No. 8,377,559, which is a division of application No. 11/699,663, filed on Jan. 30, 2007, now Pat. No. 8,053,030.

(60) Provisional application No. 60/764,151, filed on Feb. 1, 2006.

(51) Int. Cl.
| | |
|---|---|
| *A61L 31/10* | (2006.01) |
| *A61L 27/34* | (2006.01) |
| *A61L 27/50* | (2006.01) |
| *A61L 29/08* | (2006.01) |
| *A61L 29/10* | (2006.01) |
| *A61L 29/14* | (2006.01) |
| *B05D 5/08* | (2006.01) |
| *C10M 157/00* | (2006.01) |
| *C10M 157/04* | (2006.01) |
| *C10M 173/00* | (2006.01) |
| *A61L 29/04* | (2006.01) |
| *A61L 29/06* | (2006.01) |
| *B05D 5/00* | (2006.01) |
| *B05D 1/18* | (2006.01) |
| *B05D 3/06* | (2006.01) |
| *C10N 50/02* | (2006.01) |

(52) U.S. Cl.
CPC ............. *A61L 31/10* (2013.01); *A61L 27/34* (2013.01); *A61L 27/50* (2013.01); *A61L 29/041* (2013.01); *A61L 29/06* (2013.01); *A61L 29/085* (2013.01); *A61L 29/10* (2013.01); *A61L 29/14* (2013.01); *B05D 1/18* (2013.01); *B05D 3/067* (2013.01); *B05D 5/00* (2013.01); *B05D 5/08* (2013.01); *C10M 157/00* (2013.01); *C10M 157/04* (2013.01); *C10M 173/00* (2013.01); *A61L 2400/10* (2013.01); *A61L 2420/02* (2013.01); *C10M 2207/08* (2013.01); *C10M 2207/12* (2013.01); *C10M 2209/04* (2013.01); *C10M 2209/084* (2013.01); *C10M 2209/102* (2013.01); *C10M 2215/086* (2013.01); *C10M 2215/22* (2013.01); *C10M 2217/024* (2013.01); *C10M 2217/028* (2013.01); *C10M 2217/045* (2013.01); *C10N 2050/02* (2013.01); *Y10T 428/31* (2015.01); *Y10T 428/31504* (2015.04); *Y10T 428/31536* (2015.04); *Y10T 428/31551* (2015.04); *Y10T 428/31576* (2015.04); *Y10T 428/31725* (2015.04); *Y10T 428/31736* (2015.04); *Y10T 428/31935* (2015.04)

(58) Field of Classification Search
CPC .. A61L 2400/10; A61L 2420/02; A61L 27/50; A61L 29/14
See application file for complete search history.

(56) References Cited

U.S. PATENT DOCUMENTS

| | | | |
|---|---|---|---|
| 4,302,553 A | 11/1981 | Frisch et al. | |
| 4,423,099 A | 12/1983 | Mueller et al. | |
| 4,589,873 A | 5/1986 | Schwartz et al. | |
| 4,642,267 A | 2/1987 | Creasy et al. | |
| 4,840,851 A * | 6/1989 | Golander | A61L 27/34 427/307 |
| 4,872,867 A | 10/1989 | Joh et al. | |
| 4,876,126 A | 10/1989 | Takemura et al. | |
| 4,906,237 A | 3/1990 | Johansson et al. | |
| 4,990,357 A | 2/1991 | Karakelle et al. | |
| 4,994,047 A | 2/1991 | Walker et al. | |
| 5,090,406 A | 2/1992 | Gilman | |

(Continued)

FOREIGN PATENT DOCUMENTS

| | | |
|---|---|---|
| CA | 2426251 | 4/2002 |
| CN | 1106744 | 8/1995 |

(Continued)

OTHER PUBLICATIONS

European Patent No. EP 2289573B, Hollister Inc., Opposition by Coloplast A/S, Statement of Facts and Arguments dated Jul. 25, 2017.

(Continued)

*Primary Examiner* — Kai H Weng
(74) *Attorney, Agent, or Firm* — Cook Alex Ltd.

(57) ABSTRACT

This invention relates to methods of applying to a substrate a hydrophilic coating that becomes lubricious when activated with water or water vapor, and to substrates having such a hydrophilic coating.

21 Claims, No Drawings

(56) References Cited

U.S. PATENT DOCUMENTS

| | | |
|---|---|---|
| 5,264,242 A | 11/1993 | Speer |
| 5,295,978 A | 3/1994 | Fan et al. |
| 5,331,027 A | 7/1994 | Whitbourne |
| 5,576,072 A | 11/1996 | Hostettler et al. |
| 5,603,991 A | 2/1997 | Kupiecki et al. |
| 5,670,558 A | 9/1997 | Onishi et al. |
| 5,702,754 A | 12/1997 | Zhong et al. |
| 5,776,611 A | 7/1998 | Elton et al. |
| 5,804,318 A | 9/1998 | Pinchuk et al. |
| 5,871,823 A | 2/1999 | Anders et al. |
| 5,932,299 A | 8/1999 | Katoot |
| 5,984,878 A | 11/1999 | Engelson |
| 6,007,876 A | 12/1999 | Nino et al. |
| 6,017,577 A | 1/2000 | Hostettler et al. |
| 6,048,620 A | 4/2000 | Zhong et al. |
| 6,110,483 A | 8/2000 | Whitbourne et al. |
| 6,156,344 A | 12/2000 | Kim et al. |
| 6,187,369 B1 | 2/2001 | Beavers |
| 6,211,249 B1 | 4/2001 | Cohn et al. |
| 6,221,425 B1 | 4/2001 | Michal et al. |
| 6,238,799 B1 | 5/2001 | Opolski |
| 6,261,630 B1 | 7/2001 | Nazarova et al. |
| 6,291,543 B1 | 9/2001 | Shah |
| 6,340,465 B1 | 1/2002 | Hsu et al. |
| 6,540,698 B1 | 4/2003 | Ishii et al. |
| 6,629,961 B1 | 10/2003 | Israelsson |
| 6,673,385 B1 | 1/2004 | Ding et al. |
| 6,673,453 B2 | 1/2004 | Beavers et al. |
| 6,706,025 B2 | 3/2004 | Engelson |
| 6,780,504 B2 | 8/2004 | Rupprecht et al. |
| 6,828,028 B1 | 12/2004 | Fukui |
| 6,835,410 B2 | 12/2004 | Chabrecek et al. |
| 7,008,979 B2 * | 3/2006 | Schottman ............... C08K 3/22 428/411.1 |
| 7,544,381 B2 | 6/2009 | Kangas |
| 7,691,476 B2 | 4/2010 | Finley |
| 7,833,475 B2 | 11/2010 | Madsen |
| 8,052,673 B2 | 11/2011 | Nestenborg |
| 8,287,890 B2 | 10/2012 | Elton |
| 8,377,498 B2 | 2/2013 | Rindlav-Westling et al. |
| 8,512,795 B2 | 8/2013 | Dias et al. |
| 8,541,498 B2 | 9/2013 | Sandhu et al. |
| 8,747,940 B2 | 6/2014 | Lee et al. |
| 2002/0018898 A1 | 2/2002 | Opolski |
| 2002/0045049 A1 | 4/2002 | Madsen |
| 2003/0100666 A1 | 5/2003 | DeGroot et al. |
| 2004/0001892 A1 | 1/2004 | Healy et al. |
| 2004/0086722 A1 | 5/2004 | Madsen |
| 2004/0157073 A1 | 8/2004 | Burrell et al. |
| 2005/0228115 A1 | 10/2005 | Auguste et al. |
| 2006/0251694 A1 * | 11/2006 | Nielsen ................. A61L 29/085 424/422 |
| 2007/0016169 A1 | 1/2007 | Utas et al. |
| 2007/0149929 A1 | 6/2007 | Utas et al. |
| 2013/0202833 A1 | 8/2013 | Belt et al. |

FOREIGN PATENT DOCUMENTS

| | | |
|---|---|---|
| EP | 0693293 | 1/1996 |
| EP | 0379156 | 4/1996 |
| EP | 1103278 | 5/2001 |
| EP | 1745807 | 1/2007 |
| EP | 2090628 A1 | 8/2009 |
| EP | 2695636 A1 | 2/2014 |
| JP | S62500307 | 2/1987 |
| JP | 0833704 | 2/1996 |
| JP | H 08317970 | 12/1996 |
| JP | 3115590 | 12/2000 |
| WO | WO 89/09246 A1 | 10/1989 |
| WO | 9213718 | 8/1992 |
| WO | WO 94/16747 A1 | 8/1994 |
| WO | WO 95/29722 | 11/1995 |
| WO | WO-95/29722 | 11/1995 |
| WO | 9858988 | 12/1998 |
| WO | 9858990 | 12/1998 |
| WO | WO 98/58990 A1 | 12/1998 |
| WO | 9902141 | 1/1999 |
| WO | 9911728 | 3/1999 |
| WO | 9914282 | 3/1999 |
| WO | 9957201 | 11/1999 |
| WO | WO-99/056710 | 11/1999 |
| WO | 03087254 | 10/2003 |
| WO | WO 2004/056909 | 7/2004 |
| WO | WO-2006/002628 | 1/2006 |
| WO | 2006117372 | 11/2006 |
| WO | 2007011287 | 1/2007 |
| WO | WO 2013/068513 A1 | 5/2013 |

OTHER PUBLICATIONS

Preliminary Notice of Reasons for Rejection for Japanese Patent Application No. 2008-553309 dated May 21, 2013 and English translation.
Decision of the Board of Appeals dated Aug. 21, 2014 for European Application No. 10195654.8 (published as EP 1979016 on Oct. 15, 2008).
European Office Action dated Mar. 2, 2015 for European Application No. 10195654.8 (published as EP 1979016 on Oct. 15, 2008).
Canadian Office Action dated Jan. 9, 2013, for Canadian Application No. 2,641,021.
Canadian Office Action dated Feb. 17, 2014, for Canadian Application No. 2,641,021.
DuPont Packaging and Industrial Polymers, "DuPont™ Elvax® CM3326," 1995-2004.
DuPont Packaging and Industrial Polymers, "DuPont™ Nucrel® 2806," 1995-2004.
DuPont®, "Injection Moulding Guide," Hytrel® Engineering Thermoplastic Elastomer, pp. 1-24 (1997).
DuPont®, "Rheology and Handling," Product Information, pp. 1-8 (1993).
DuPont™ Nuclei®, "DuPont™ Nucrele", Retrieved from the Internet on Jan. 17, 2007: URL:http://www/2.dupont.com/Products/en_RU/Nucrel_en.html.
Noveon the Speciality Chemicals Innovator™, "Noveon's Family of TPUs.".
Noveon the Speciality Chemicals Innovator™, "Thermedics™ Polymer Products," Retrieved from the Internet on Jan. 17, 2007: URL:http://www.estane.com/relatedProducts/ThermedicsOverview.asp.
Noveon the Speciality Chemicals Innovator™, "Overview," Product Information, Estane® Thermoplastic Polyurethane TPU, Retrieved from the Internet on Jan. 17, 2007: URL:http://www.estane.com/featuresBenefits/overview.asp.
Pebax Basis of Performance, "What are PEBAZ® Breathable Films?" Breathable films, pp. 1-7 (2002).
Sartomer, "Applicable Product Line(s)," Retrieved from the Internet on Jan. 17, 2007: URL:http://www.sartomer.com/prodselectview.asp?sa=1&api=2&plid=3&sgid=27.
Sartomer, "Oligo (2-Hydroxy-2-Methyl-1-4 (1-Methylvinyl) Propanone and 2-Hydroxy-2-Methyl-1-Phenyl Propan-1-One (Monomeric)," Product Bulletin: Esacure KIP 150, p. 1.
Sartomer, "Product Detail: Esacure KIP 150," Retrieved from the Internet on Jan. 16, 2008: URL:http://www.sartomer.com/proddetail.asp?plid=3&sgid=27&prid=ESACURE+KIP+150.
Ward, "Medical Plastics Thermoplastic Silione-Urethane Copolymers: A New Class of Biomedical Elastomers," Medical Device Link (2000), Retrieved from the Internet on Jan. 11, 2008: URL:http://www.devicelink.com/mddi/archive/00/04/0011.html.
International Preliminary Report on Patentability for International Application No. PCT/US2007/002545,dated Aug. 5, 2008,
International Search Report for International Application No. PCT/US2007/002545, dated Jun. 9, 2008.
Written Opinion for International Application No. PCT/US2007/002545, dated Jun. 9, 2008.
European Office Action for European Application No. 07762800.6, dated Oct. 13, 2009.

(56) References Cited

OTHER PUBLICATIONS

European Office Action for European Application No. 07762800.6, dated Dec. 23, 2008.
Decision to refuse European patent application for corresponding European Patent Application No. 07762800.6, dated Jul. 13, 2011.
Summons and Annex for Oral Proceedings dated Oct. 7, 2010, for European Patent Publication No. EP 1979016 from the European Patent Office.
Minutes of the Oral Proceeding held Mar. 29, 2011, for European Patent Publication No. Ep 1979016 from the European Patent Office dated Apr. 26, 2011.
Notice of Opposition dated Mar. 31, 2016 for European Patent Publication No. EP 1979016 from the European Patent Office.
Notice of Opposition dated Apr. 1, 2016 for European Patent Publication No. EP 1979016 from the European Patent Office.
Summons and Annex for Oral Proceedings dated Jan. 26, 2017, for European Patent Publication No. Ep 1979016 from the European Patent Office.
Letter Regarding the Opposition Procedure dated Aug. 21, 2017, for European Patent Publication No. Ep 1979016 from the European Patent Office.
Scanned Annex to a Communication Opposition Procedure dated Nov. 24, 2017, for European Patent Publication No. EP 1979016 from the European Patent Office.
Provision of Minutes Regarding Opposition Procedure dated Nov. 24, 2017, for European Patent Publication No. EP 1979016 from the European Patent Office.
Grounds for Opposition Decision dated Nov. 24, 2017, for European Patent Publication No. EP 1979016 from the European Patent Office.
Decision Revoking the European Patent dated Nov. 24, 2017, for European Patent Publication No. EP 1979016 from the European Patent Office.
Decision with Annex of the Opposition Division and Instruction dated Nov. 24, 2017, for European Patent Publication No. EP 1979016 from the European Patent Office.
Estane® Thermoplastic Polyurethane Tpu, "Product Information," Retrieved from the Internet on Jan. 17, 2007: <URL:http://www.estane.com/featuresBenefits/overview.asp>.
European Search Report and Written Opinion dated Apr. 19, 2011, for European Patent Publication No. EP 2289573.
European Office Action dated Jan. 16, 2013, for European Patent Publication No. EP 2289573.
European Office Action dated Mar. 2, 2015, for European Patent Publication No. EP 2289573.
Observations Concerning Appeal filed in EP1979016—dated Aug. 14, 2018.
Opposition-appeal against EP 1979016 filed in EP1979016—dated Aug. 15, 2018.
Opponent Submission filed in EP 2289573—dated Jul. 17, 2019.
Decision Revoking European Patent No, 2289573—dated Nov. 13, 2018.
Opponent Submission filed in EP 2289573—dated Aug. 21, 2018.
Summons to Attend Oral Proceedings in EP 2289573—dated Mar. 14, 2018.

\* cited by examiner

METHODS OF APPLYING A HYDROPHILIC COATING TO A SUBSTRATE, AND SUBSTRATES HAVING A HYDROPHILIC COATING

CROSS-REFERENCE TO RELATED APPLICATION

This application is a continuation of U.S. patent application Ser. No. 13/748,842, filed Jan. 24, 2013, which is a continuation of U.S. patent application Ser. No. 13/243,942, filed Sep. 23, 2011, now U.S. Pat. No. 8,377,559 which is a division of U.S. patent application Ser. No. 11/699,663, filed Jan. 30, 2007, now U.S. Pat. No. 8,053,030, which claims the benefit of U.S. Provisional Application No. 60/764,151, filed Feb. 1, 2006, all of the above of which are incorporated by reference.

FIELD OF THE INVENTION

This invention relates to methods of applying to a substrate a hydrophilic coating that becomes lubricious when activated with water or water vapor, and to substrates having such a hydrophilic coating.

BACKGROUND

In the medical field, and in other fields as well, there has developed a need for substrates with surfaces that become lubricious upon contact with water. A main use of lubricious materials involves catheters, catheter guide wires, and other medical devices that are meant to be inserted into the body. The lubricious nature of such materials allows the insertion (and subsequent removal) of a catheter or other medical device to be accomplished with minimum resistance, thereby reducing discomfort and possible injury.

In many cases, it is easy to prepare a functional lubricious coating for a substrate surface. However, it is more difficult to prepare a lubricious coating that is securely anchored to the substrate surface. Secure anchoring of a lubricious coating to a substrate surface is generally desirable, and particularly useful in the medical field, where secure anchorage of the coating is often an important requirement.

U.S. Pat. No. 4,642,267 to Creasy et al. discloses a hydrophilic polymer blend comprising a thermoplastic polyurethane and a poly(N-vinyl lactam). When used as a coating material, the polymer blend components are co-dissolved in an organic solvent capable of solubilizing both polymers, a substrate is dip coated in the solution, and the solvent is then driven off by a drying process so as to form a hydrophilic coating on the substrate surface. However, the coating attachment to the substrate is considered to lack the security desired. Another disadvantage of the '267 patent is that high boiling point and potentially toxic solvents are used to deliver the coating formulation, and thus significant costs must be incurred to drive off the solvent residuals from the coated product so as to obtain the desired biocompatibility.

U.S. Pat. No. 5,702,754 to Thong discloses coating a substrate surface with a polymer having reactive functional groups and an excess of cross-linking agent. The polymer is cured to form a coating. Then, a second coating comprising a hydrophilic polymer having the same type of reactive functional groups is applied thereover. When the hydrophilic polymer is then cured, the second coating becomes covalently bonded to the first coating because the first coating includes an excess of cross-linking agent thereby permitting covalent bonding between the first coating and the hydrophilic polymer. Disadvantages of this approach include the fact that multiple steps are required and multiple polymer solutions are involved. There are also significant limitations in the selection of lubricious polymers and cross-linking agents.

SUMMARY OF THE INVENTION

In one aspect, the invention provides a method of applying a hydrophilic coating to a substrate having a surface comprised at least in part of a water-swellable material, and contacting the substrate surface with a solution comprising at least one of (i) a water-soluble polymer capable of being cross-linked to form a cross-linked, lubricious, hydrophilic coating and (ii) a water-soluble monomer capable of being polymerized to form a cross-linked, lubricious, hydrophilic coating. The water-soluble polymer can be cross-linked in the presence of the swollen substrate surface to provide a cross-linked coating that is entangled with and securely anchored to the substrate surface. Similarly, the monomer can either form a crosslinked hydrogel network as it is polymerized, or can be polymerized and then subsequently cross-linked, in the presence of the swollen substrate surface, to provide a cross-linked coating that is entangled with and securely anchored to the substrate surface. The substrate includes a first or outer layer comprising a water-swellable material. The substrate may further include an optional second or support layer, which comprises non-water-swellable materials and/or water-swellable materials.

In another aspect, the invention provides a substrate having a hydrophilic coating, such substrate, prior to coating, having a surface comprised at least in part of a water-swellable material having swollen and non-swollen states, and the coating comprises an interpenetrating polymer network disposed on at least a part of the surface, the interpenetrating polymer network formed by at least one of (i) a water-soluble polymer capable of being cross-linked to form a cross-linked, lubricious, hydrophilic coating and (ii) a water-soluble monomer capable of being polymerized to form a cross-linked, lubricious, hydrophilic coating, in the presence of the swollen state of the surface, so as to secure the hydrophilic coating to the surface.

DETAILED DESCRIPTION

One aspect of the invention relates to methods of applying a lubricious, hydrophilic coating to a substrate. An additional aspect of the invention relates to substrates having such a lubricious, hydrophilic coating.

As used herein, the term "lubricious coating" refers to a coating that provides a substrate surface having a coefficient of friction value less than about 0.3, less than about 0.1, and/or less than about 0.05, for example, 0.03, or even 0.01.

The invention involves creating an interpenetrating polymer network in situ on a substrate surface. For example, a substrate surface comprising a water-swellable material is contacted with a solution comprising a water-soluble hydrophilic polymer capable of being cross-linked to form a cross-linked, lubricious hydrophilic coating. Alternatively, a water-soluble monomer, either capable of being polymerized to form a cross-linked, lubricious, hydrophilic coating, or of being polymerized and then cross-linked to form a cross-linked, lubricious, hydrophilic coating, may be used in place of, or in addition to, the water-soluble hydrophilic polymer. The coating is typically then cured, for example, by exposure to UV light, in order to cross-link the water-soluble polymer and/or polymer formed from the water-soluble monomer.

The use of one or more water-soluble polymers is typically preferred relative to the use of one or more water-soluble monomers, however, particularly for medical applications, because residual unpolymerized monomer can present biocompatibility issues for medical device applications.

Because the water-swellable material of the substrate swells in the presence of water and/or alcohol, it is believed to become physically entangled with the water-soluble hydrophilic polymer before cross-linking, and those entanglements are locked in during cross-linking. Thus, a coating comprising the interpenetrating polymer network is formed by polymerizing the water-soluble polymer in the presence of the water-swellable substrate surface when the water-swellable substrate surface is in a swollen state, and results in the lubricious coating being securely anchored to the substrate (after cross-linking thereof). Essentially, the method allows two hydrogels to be linked together mechanically on a molecular scale.

Advantageously, the hydrophilic coating can be secured to the surface without the need for covalent interactions between the hydrophilic coating and the first layer. Another advantage is that the coating formulation can be carried using solvents such as water and lower alcohols, which are inexpensive, biocompatible, and relatively easy to drive off from the coated product. Still another advantage is the versatility of the invention; the invention will provide secure anchorage for any hydrophilic coating formed from a water-soluble polymer and/or water-soluble monomer, which can be coated from an aqueous or alcohol based solution, without the need for a primer layer or other polymer solution based anchorage means. This versatility allows a wide number of polymer/cross-linking agent systems and/or monomer/initiator/cross-linking systems to be utilized, and thus for an optimal system to be implemented for any given application.

In one embodiment, the terms "well-anchored" or "securely anchored" refers to a coating that, after an abrasion protocol is conducted on the substrate carrying the coating, results in a substrate having a final coefficient of friction value, when the coating is activated, for example, by water immersion, that is not more than ten times, not more than five times, and/or not more than two times the original coefficient of friction value prior to abrasion. A suitable abrasion protocol includes passing a coated tube through a hole which is about 10% smaller diameter than the outside diameter of the tubing 100 times, while keeping the coating wet during the abrasion cycles. After this abrasion protocol, the tube is immersed in deionized water for about 30 seconds so as to activate the coating, and the coefficient of friction can be determined using standard means.

A substrate, such as a catheter tube, to be coated by the methods of this invention, is formed in a way that provides it with a surface or surface layer comprised at least in part of a water-swellable material. That may be accomplished in a variety of ways including but not limited to coextruding a substrate having a first or outer layer comprising any suitable water-swellable material, and a second or inner support layer comprised of non-water-swellable materials and/or water-swellable materials.

Generally, any water swellable-materials or mixtures thereof could be used for the first or outer layer. Suitable water-swellable materials include but are not limited to water-swellable polyamide-based copolymers, water-swellable polyester-based copolymers, water-swellable urethane-based copolymers, and mixtures thereof. Any of a variety of thermoplastic polymers, thermoplastic elastomers, and/or thermoplastic alloys, which are capable of swelling in the presence of water (e.g., an aqueous solution) may be used. In general, such water swellable polymers will also swell in lower alcohols such as methanol, ethanol, propanol, isopropanol, butanol, and the like. Higher alcohols such as hexanol and octanol may also be used, but lower alcohols are typically preferred because of their increased volatility relative to water.

Preferably, the first layer is comprised of a water-swellable thermoplastic elastomer comprising a block copolymer having rigid and flexible blocks. Suitable rigid blocks include polyamide blocks, polyester blocks, and polyurethane blocks, but other rigid polymer blocks may be used. The rigid block is preferably either glassy or crystalline at room temperature. Suitable flexible blocks include flexible polyether blocks such as flexible polyethylene oxide blocks, flexible poly-N-vinyl lactam blocks such as flexible polyvinylpyrrolidone blocks, flexible polyalcohol blocks, and flexible polyacid blocks. Of course, other flexible blocks could also be used.

Suitable water-swellable thermoplastic elastomers include but are not limited to polyether/polyamide block elastomers such as those sold under the PEBAX® trade name (Arkema, Pa.), for example, such as PEBAX® 1647, PEBAX® 1074, and PEBAX® MX1652, and polyester elastomers such as those sold under the HYTREL® trade name (Du Pont de Nemours, Del.), for example, such as HYTREL® 8171 and HYTREL® 8206. Other suitable water-swellable thermoplastic elastomers include but are not limited to thermoplastic polyurethanes such as polyether thermoplastic polyurethanes sold under the ESTANE® and the TECOPHILIC® trade names (Noveon Inc., OH) and polyester thermoplastic polyurethanes such as those sold under the ESTANE® and CARBOTHANE® trade names (Noveon Inc., OH).

The substrate can be made entirely from a water-swellable material. Polymer blends including at least one water-swellable material can alternatively be used. Surprisingly, even polymer blends where a water-swellable material comprises only a minority of the polymer blend will provide securely anchored hydrophilic coatings. This allows flexibility in designing substrates, for example, as a homoextrusion that will have the mechanical properties needed for a given application. For example, tubing made of 40 weight percent (wt. %) PEBAX® 1074 (a water-swellable thermoplastic elastomer) and 60 wt. % PEBAX® 3533 (a non-water-swellable thermoplastic elastomer) has desirable properties for a urinary catheter application, and provides many or all of the advantages of this invention.

Alternatively, the substrate can have an outer layer made from a water-swellable material, or an outer layer made from a blend comprised of water-swellable and non-water-swellable materials. The substrate can then have an inner or support layer comprised of one or more non-water-swellable materials. Of course, the inner or support layer may be made from or further include one or more water-swellable materials.

As used herein, the term "water-swellable" generally refers to a material that swells in the presence of water or alcohol. In various embodiments, the term refers to a material that increases in at least one dimension by at least 0.5%, at least 1%, at least 2%, at least 5%, at least 10%, at least 25%, or even greater when immersed in water for a period of approximately 90 minutes. In accordance with the foregoing embodiments, a 1 inch by 1 inch by 1 mil square of material can be immersed in water for a period of 90 minutes, and the increase in the height or length can be determined relative to the original height or length so as to ascertain whether a certain material swells sufficiently to be considered a water-swellable material in accordance with the invention. If so, the material can generally be considered suitable for use as a water-swellable material in the invention.

Generally, any material can be used in forming the optional second or support layer, but materials capable of being extruded or otherwise melt-processed are generally preferred. Suitable materials for use in the optional second or support layer include but are not limited to thermoplastic resins, such as, for example, olefin polymers, particularly, polyethylenes, polypropylenes, polyvinylchlorides, polytetrafluoroethylenes, polyvinylacetates, polystyrenes, polyesters, polyurethanes, polyamides, other suitable polymers, and mixtures thereof. Metals, ceramics, and other materials may also be used as the support layer, but then the outer layer needs to be affixed or coupled to the second layer by a mechanism different than co-extrusion, for example, by spin-casting, dip-coating, wire extrusion coating, or otherwise affixing, coupling, or adhering the water-swellable surface layer (or substrate comprising same) to the second layer.

The substrate can be a medical device. Exemplary medical devices that may be coated with the lubricious coatings in accordance with the invention include but are not limited to contact lenses, medical implants including but not limited to pacemakers and wire leads for same, intravascular implants including but not limited to arterial stents, and catheters including but not limited to urinary catheters, fecal catheters, catheters for administration of intravenous fluids, medications, and nutrition, and coronary catheters such as angioplasty catheters. Further still, in certain medical device applications it may be desirable to incorporate a drug into the coating solution, or to add a drug after formation of the coating on the medical device. For example, stents having a coating in accordance with the invention can comprise a drug, for example, taxol to prevent late stenosis, or heparin to prevent the formation of a thrombus.

Additionally, non-medical device applications of the invention can also be envisioned where surfaces having a low coefficient of friction in a wet environment are desired because the invention can provide a highly lubricious coating to any product that is used in a wet environment. Possible non-limiting examples include marine uses, for example, such as wet suits or boat hulls where the coating could be applied to reduce drag.

The untreated substrate is typically dipped or otherwise coated with a polymer solution in which the coating polymer is dissolved in water, alcohol, or a solution containing both water and alcohol. If a catheter is being coated, a mandrel can be inserted into the catheter structure in order to prevent any coating solution from contacting and/or coating the inside of the catheter when the coating solution is applied.

Any suitable hydrophilic polymer capable of being cross-linked and of swelling and becoming lubricious when exposed to water or water vapor may be used to provide the hydrophilic coating. Upon being cross-linked, the network of the coating polymer forms an interpolymer with the swollen water-swellable material, for example, with the flexible (or soft) blocks of the substrate surface block polymer, resulting in a coating that is securely anchored to the substrate. Suitable water-soluble hydrophilic polymers include but are not limited to polyacrylic acids, acrylic acid copolymers such as acrylamide/acrylic acid copolymers, polyvinylpyrrollidones, polyvinylalcohols, water-soluble polymers containing carboxylic acid functional groups, and mixtures thereof. Other water-soluble polymers that can be cross-linked to form a hydrophilic coating may also be used.

Similarly, any suitable hydrophilic monomer capable of being polymerized to form a cross-linked network and becoming lubricious when exposed to water or water vapor may be used to provide the hydrophilic coating. Suitable water-soluble hydrophilic monomers that can be used include but are not limited to vinyl monomers, for example, vinyl alcohols, vinylpyrrollidones, acrylamides, methacrylates, acrylic acids, and mixtures thereof. Some of these can be copolymerized with multifunctional monomer to form a network in situ, others can be polymerized and subsequently cross-linked using methods well known in the art. Various initiators, for example, photoinitiators including but not limited to benzophenone can be used to polymerize the monomers.

An important advantage of this method is that it is relatively easy to prepare a substrate with a securely anchored hydrophilic coating. Since the outer layer of the substrate generally includes a thermoplastic polymer, known manufacturing methods that are uncomplicated, direct, and economical, such as extrusion, co-extrusion, or injection molding, may be used to produce a substrate having a water-swellable surface. The coating method is applicable to any system of hydrophilic coating polymer and cross-linking method that can be achieved using a water- or alcohol-based solvent system. Similarly, the coating method is applicable to any system of hydrophilic monomer, initiator, and cross-linking method that can be achieved using a water- or alcohol-based solvent system.

Suitable cross-linking agents are well known in the art and include but are not limited to UV activatable cross-linking agents, carbodiimides, aziridines, melamine formaldehydes, and multifunctional carboxylic acid cross-linking agents. Exemplary UV activatable cross-linking agents include polymeric hydroxyl ketones sold under the ESACURE™ trade name (Sartomer Company, PA), for example, ESACURE™ KIP 150 and ESACURE™ ONE. Exemplary carbodiimide cross-linking agents are sold under the CARBODILITE™ trade name (Nisshinbo Industries, Inc., JP), for example, CARBODILITE™ V-02-L2 and CARBODILITE™ E-02. Exemplary aziridine cross-linking agents are sold under the cross-linker CX-100 trade name (DSM Neo-Resins, DSM, NL). Heat and/or light can also be used to cross-link some water-soluble polymers.

The methods of applying a hydrophilic coating to a substrate and substrates having such a hydrophilic coating in accordance with the invention can be better understood in light of the following examples. However, the foregoing description and the following examples are merely illustrative, and therefore no unnecessary limitations should be understood therefrom as numerous modifications and variations are expected to occur to those skilled in the art.

Example 1

A coating polymer solution was prepared in an approximately 70:30 weight/weight isopropyl alcohol/water solvent system, where the polymer was polyvinylpyrrolidone K-90 at about 9 wt./vol. Included in the solution was about 0.03 wt. % UV activatable cross-linking agent (ESACURE™ KIP 150, Sartomer).

A thermoplastic substrate was employed in the form of a coextruded tube having an outside diameter of about 0.180 inches and an inside diameter of about 0.123 inches. The tube had an outer layer of about 0.003 inches thick that was a blend of a polyether/polyamide block elastomer (PEBAX® 1074, a water-swellable thermoplastic elastomer available from Arkema, Pa.) with an ethylene acid copolymer resin (NUCREL® 2806, a non-water-swellable thermoplastic elastomer available from Du Pont de Nemours, Del.) at a weight ratio of about 40:60. The inner layer of the tube was a blend of thermoplastic, non-water-swellable resins designed to give the desired mechanical properties to the overall tube structure. The tube was dipped in the coating solution and held therein for about 10 minutes prior to withdrawal. After withdrawal, the tube was air dried for about 30 minutes. Thereafter, the coated tube was exposed to UV light for about 5 minutes.

The tube with its cured coating was immersed in deionized water for 30 seconds. At that point, the surface of the tube was found to be highly lubricious, and the lubricious coating was securely adhered to the tube.

Example 2

Another approach is to use a separate, second solution that contains a cross-linking agent for the coating polymer. The second solution can be applied to the substrate having a water-swellable outer surface either before, or after, the coating polymer solution is applied. After both solutions have been applied, the coating is then cross-linked.

A coextruded tube was prepared having an outer layer of a polyether/polyamide block elastomer (PEBAX® 1074, Arkema, Pa.), and an inner layer of a polyether/polyamide block elastomer (PEBAX® 2533, a non-water-swellable thermoplastic elastomer available from Arkema, Pa.). The tube was first dipped in an approximately 70:30 weight/weight isopropyl alcohol/water solution containing about 12 wt. % of a carbodiimide cross-linking agent (CARBODILITE™ V-02-L2, Nisshinbo, Japan), and held therein for ten minutes prior to withdrawal. The tube was then air dried for ten minutes, subsequently dipped in an approximately 70:30 weight/weight isopropyl alcohol/water solution containing about 7.5 wt. % of a water-soluble polymer containing carboxylic acid functional groups (GANTREZ™ S-97BF, ISP Technologies, Inc.), and then withdrawn immediately. After withdrawal, the tube was air dried for ten minutes.

The water-soluble polymer of this example is a methyl vinyl ether copolymer with maleic anhydride where the anhydride has been hydrolyzed into a diacid. The acid groups can be cross-linked by the carbodiimide cross-linking agent.

Curing was accomplished by heating the tubing to approximately 70° C. for about 20 minutes in a conventional oven. The coating was neutralized by dipping it in a buffer solution. The resulting tube with its cured coating was then dipped in deionized water for 30 seconds. The surface of the wetted tube was slippery and the coating was securely adhered to the tube.

Example 3

A thermoplastic substrate was employed in the form of a coextruded tube having an outside diameter of about 0.181 inches and an inside diameter of about 0.122 inches. The tube had an outer layer of about 0.003 inches thick, with the inner layer accounting for the balance of the tube. The inner tube layer comprised a blend of an ethylene octene copolymer (EXACT™ 5371, ExxonMobil Chemical Company, ExxonMobil, Tex.) with an ethylene acid copolymer resin (NUCREL® 2806, Du Pont de Nemours, Del.) at a weight ratio of approximately 20:80, and the outer tube layer comprised a blend of a polyether/polyamide block elastomer (PEBAX® 1074, Arkema, Pa.) with an ethylene acid copolymer resin (NUCREL® 2806, Du Pont de Nemours, Del.) at a weight ratio of approximately 40:60.

The tubing was coated by dipping in an approximately 70:30 weight/weight isopropyl alcohol/water solution containing about 5.5 wt. % polyvinylpyrollidone K-90 (ICI Chemicals, England) and about 0.11 wt. % ESACURE™ One (Sartomer, Pa.). The tubing was held in the coating solution for about 5 minutes in this solution and then withdrawn. After withdrawal, the coated tubing was air dried for about 50 minutes (at room temperature). Thereafter, the coated tube was exposed to UVC light for approximately 2.5 minutes.

The resulting tube with its cured coating was then immersed in deionized water for about 30 seconds. At that point, the surface of the tube was found to be highly lubricious, having an average coefficient of friction (n=12 samples tested) of about 0.02.

To test coating anchorage to the substrate tubing, an abrasion testing protocol was performed on the resulting coated tubing. The sample was passed through a hole in a 1/32" thick silicone rubber sheet, with the hole being about 10% smaller diameter than the outside diameter of the tubing. This was done 100 times, keeping the coating wet during the abrasion testing. After this abrasion protocol, the tube was again immersed in deionized water for about 30 seconds and tested for coefficient of friction. Again, the average coefficient of friction for the samples was about 0.02.

Another group of samples was immersed for about 30 seconds in water to activate the coating, and then allowed to stand out in open air for about 10 minutes. Following this drying protocol, the average coefficient of friction (n=12 samples tested) was about 0.02.

Still another group of samples (n=three samples) were subjected to a thermoforming process to create a bullet shaped closed tip on one end in order to make a tipped tube suitable for use as a urinary catheter. This tipped tubing was subjected to a coating process as described in this example above, except the cure was by accomplished by exposure to UVC light for a period of about 3 minutes. After immersion in deionized water for about 20 minutes, the surface of the coated tubing was very slippery and the slippery coating was well adhered to both the formed tip portion of the tubing and the straight wall portion of the tubing.

The foregoing examples demonstrate several advantages of the invention. For example, highly lubricious, highly adherent coatings have been achieved with two different water soluble polymer/cross-linker systems, and with three different substrate constructions. Example 3 further demonstrates that it is possible to thermoform a multi-layered tube while maintaining the water-swellable properties of the outer layer surface, which allows a securely anchored coating to be achieved, even in the formed portion of the substrate. Example 3 also demonstrates that coatings made per this invention are able to maintain their slippery nature even after an extended period of air exposure. It is theorized that the water-swellable nature of the substrate surface helps in this regard, as the substrate surface will hold water and thus perhaps contribute to the ability of the coating to maintain hydration and therefore lubricity. This attribute of the invention is particularly advantageous for intermittent urinary catheters.

While embodiments of this invention have been disclosed in considerable detail herein for purposes of illustration, it will be understood by those skilled in the art that many of those details may be varied without departing from the spirit and scope of the invention. Accordingly, only such limitations as appear in the appended claims should be placed on the invention.

What is claimed is:

1. A method of applying a hydrophilic coating on an uncoated surface of a catheter tube, the method comprising:
   contacting said uncoated surface of the catheter tube with a solution, the uncoated surface comprising a blend of a water-swellable polymer and a separate non-water-swellable polymer, wherein the solution swells water swellable polymer, the solution comprising water and at least one of (i) a water-soluble polymer capable of being cross-linked to form a cross-linked, lubricious, hydrophilic coating and (ii) a water-soluble monomer capable of being polymerized to form a cross-linked, lubricious, hydrophilic coating, and
   forming the cross-linked, lubricious, hydrophilic coating on the surface of the catheter tube.

2. The method of claim 1, wherein the solution further comprises alcohol.

3. The method of claim 1, wherein the catheter tube comprises a coextruded tube having a first layer, and a second layer, wherein the first layer defines the uncoated surface.

4. The method of claim 3, wherein the second layer comprises a non-water-swellable polymer.

5. The method of claim 1, wherein the water-swellable polymer comprises a block copolymer.

6. The method of claim 5, wherein the block copolymer is selected from the group consisting of water-swellable polyimide-based copolymers, water-swellable polyester-based copolymers, water-swellable urethane-based copolymers, and mixtures thereof.

7. The method of claim 1, wherein the water-soluble polymer is selected from the group consisting of polyacrylic acids, acrylic acid copolymers, poly-N-vinyl lactams, polyvinylalcohols, polyvinylalcohol copolymers, and mixtures thereof.

8. The method of claim 7, wherein the poly-N-vinyl lactam comprises polyvinylpyrollidone.

9. The method of claim 1, wherein the water-soluble monomer is selected from the group consisting of vinyl alcohols, vinylpyrollidones, acrylamides, methacrylates, acrylic acids, and mixtures thereof.

10. The method of claim 1, wherein the solution further comprises a cross- linking agent.

11. The method of claim 10, further comprising curing the water-soluble polymer.

12. The method of claim 10, wherein the cross-linking agent is selected from the group consisting of UV activatable cross-linking agents, carbodiimides, aziridines, melamine formaldehydes, and multifunctional carboxylic acid cross-linking agents.

13. The method of claim 1, further comprising contacting the uncoated surface of the catheter tube with a solution comprising a cross-linking agent.

14. The method of claim 1 further including bringing the uncoated surface of the catheter tube out of contact with the solution and drying the surface of the catheter tube prior to forming the cross-linked, lubricious, hydrophilic coating.

15. The method of claim 1 wherein contacting the uncoated surface of the catheter tube with solution comprises dip coating the catheter tube to apply the solution to the uncoated surface.

16. The method of claim 1 wherein forming the cross-linked, lubricious, hydrophilic coating is conducted in the present of the swollen water-swellable polymer of the surface of the catheter tube.

17. The method of claim 1 wherein the water-swellable polymer comprises a polymer that increases in at least one dimension by at least 0.5% when immersed in water for a period of approximately 90 minutes.

18. The method of claim 1, wherein the water-swellable polymer is less than 50 wt% of the blend.

19. The method of claim 1, wherein the blend comprises 40 wt% of the water-swellable polymer and 60 wt% of the non-water-swellable polymer.

20. A method of applying a hydrophilic coating on an uncoated surface of a catheter tube, the method comprising:
   contacting the uncoated surface of the catheter tube with a solution, the uncoated surface comprising a blend of a water-swellable polymer and a separate non-water-swellable polymer, wherein the solution swells the water-swellable polymer, the solution comprising water and a water-soluble polymer capable of being cross-linked to form a cross-linked, lubricious hydrophilic coating, wherein the polymer becomes entangled with the water-swellable polymer of the surface of the catheter tube; and
   cross-linking the water-soluble polymer, whereby the crosslinked water-soluble polymer and the water-swellable polymer of the surface of the catheter tube become linked together mechanically on a molecular scale to form a lubricious, hydrophilic coating securely anchored to the surface of the catheter tube.

21. A method of attaching a hydrophilic coating on an uncoated surface of a catheter tube, the method comprising:
   contacting the uncoated surface of the catheter tube with a solution, the uncoated surface comprising a blend of a water-swellable polymer and a separate non-water-swellable polymer, wherein the solution swells the water-swellable polymer, the solution comprising water and a water-soluble monomer capable of being polymerized to form a water soluble polymer, the monomer becoming dispersed within the water-swellable polymer of the surface of the catheter tube;
   polymerizing the monomer to form the water soluble polymer; and
   cross-linking the water-soluble polymer, whereby the crosslinked water-soluble polymer and the water-swellable polymer of the surface of the catheter tube become linked together mechanically on a molecular scale, to form a lubricious, hydrophilic coating securely anchored to the surface of the catheter tube.

* * * * *